United States Patent
Smith et al.

(10) Patent No.: US 10,285,588 B2
(45) Date of Patent: *May 14, 2019

(54) MECHANICAL SUPPORT OF AN INDIRECT CONTACT LENS BY A SURGICAL MICROSCOPE DURING VITREORETINAL SURGERY

(71) Applicant: NOVARTIS AG, Basel (CH)

(72) Inventors: Ron Smith, Lake Forest, CA (US); Tammo Heeren, Lake Forest, CA (US); Steve Charles, Memphis, TN (US)

(73) Assignee: Novartis AG, Basel (CH)

(*) Notice: Subject to any disclaimer, the term of this patent is extended or adjusted under 35 U.S.C. 154(b) by 0 days.

This patent is subject to a terminal disclaimer.

(21) Appl. No.: 15/846,464

(22) Filed: Dec. 19, 2017

(65) Prior Publication Data

US 2018/0103844 A1    Apr. 19, 2018

Related U.S. Application Data

(62) Division of application No. 14/731,055, filed on Jun. 4, 2015, now Pat. No. 9,854,969.

(51) Int. Cl.
| | | |
|---|---|---|
| A61B 3/13 | (2006.01) | |
| A61B 3/125 | (2006.01) | |
| A61B 90/20 | (2016.01) | |

(52) U.S. Cl.
CPC ............ *A61B 3/13* (2013.01); *A61B 3/125* (2013.01); *A61B 90/20* (2016.02)

(58) Field of Classification Search
CPC ........... A61B 3/13; A61B 3/125; A61B 90/20; A61F 9/00–9/0136
USPC ....................... 359/381; 606/4; 351/219, 246
See application file for complete search history.

(56) References Cited

U.S. PATENT DOCUMENTS

| | | | |
|---|---|---|---|
| 4,856,872 | A | 8/1989 | Spitznas et al. |
| 5,336,215 | A | 8/1994 | Hsueh |
| 5,793,524 | A | 8/1998 | Luloh |
| 7,092,152 | B2 | 8/2006 | Kirchhuebel |
| 7,940,455 | B2 | 5/2011 | Gaida |
| 9,089,401 | B2 | 7/2015 | Raksi |
| 9,854,969 | B2 * | 1/2018 | Smith ...................... A61B 3/13 |

OTHER PUBLICATIONS

Roger N. Clark, "Notes on the Resolution and Other Details of the Human Eye" ClarkVision.com, available at http://clarkvision.com/articles/eye-resolution.html; 5 pages, Nov. 25, 2009.
"LC 2012 Spacial Light Modulator (transmissive)", HOLOEYE Photonics AG, product page available at http://holoeye.com/spatial-light-modulators/lc-2012-spatial-light-modulator/, 4 pages.
(Continued)

*Primary Examiner* — Zachary W Wilkes

(57) ABSTRACT

An indirect contact lens is mechanically coupled to a surgical microscope during ophthalmic surgery, such as vitreoretinal surgery. The indirect contact lens rests on a cornea of an eye of a patient during the surgery but is supported by a surgical microscope attachment having multiple degrees of freedom to accommodate small movements of the eye while remaining aligned to an optical axis of the surgical microscope.

12 Claims, 3 Drawing Sheets

(56) References Cited

OTHER PUBLICATIONS

Holoeye Photonics AG, "SLM: Spatial Light Modulators Manual", available at http://holoeye.com/wp-content/uploads/Spatial_Light_Modulators.pdf, 4 pages, 2012.
Volk Optical, Inc., "Volk 40D BIO Lens", product page available at www.volk.com/index.php/40d.html, 2 pages, 2014.
Volk Optical, Inc., "Flat SSV ACS®", product page available at www.volk.com/index.php/flat-ssy-aesr.html, 2 pages, 2014.
Volk Optical Inc., "MERLIN Surgical System Brochure", available at http://volk.com/pdf/merlinbrochure2011.pdf, 4 pages, Mar. 20, 2010.
Volk Optical Inc., "MERLIN Surgical System Operator's Manual", available at http://www.volk.com/pdf/IM-039/IM-039%20-%20English.pdf, 27 pages, Dec. 14, 2010.
Volk Optical, Inc., "Volk SuperQuad 160", product page available at www.volk.com/index.php/superquad-160.html, 3 pages, 2014.
Oculus Surgical, Oculus BIOM 5: Binocular Indirect Ophthalmomicroscope, product page available at http://www.oculussurgical.com/us/products/oculus-biom-5/highlights, 13 pages, 2015.
Oculus, Oculus Biom 3m, product page and machine translation available at http://www.microsofttranslator.com/by.aspx?ref=SERP&br=ro&mkt=en-US&dl=en&lp=FR_EN&a=http%3a%2f%2fwww.oculus.de%2ffr%2fsites%2fdetail_ger.php%3fpage%3d472, 1 page, 2014.
"Mounting Components," ThorLabs Catalog, N.p.: ThorLabs, 2002, p. 23.

\* cited by examiner

MECHANICAL SUPPORT OF AN INDIRECT CONTACT LENS BY A SURGICAL MICROSCOPE DURING VITREORETINAL SURGERY

This application is a divisional of U.S. patent application Ser. No. 14/731,055 filed Jun. 4, 2015, the contents of which is herewith incorporated by reference in its entirety.

BACKGROUND

Field of the Disclosure

The present disclosure relates to ophthalmic surgery, and more specifically, to mechanical support of an indirect contact lens by a surgical microscope during vitreoretinal surgery.

Description of the Related Art

In ophthalmology, eye surgery, or ophthalmic surgery, is performed on the eye and accessory visual structures. More specifically, vitreoretinal surgery encompasses various delicate procedures involving internal portions of the eye, such as the vitreous humor and the retina. Different vitreoretinal surgical procedures are used, sometimes with lasers, to improve visual sensory performance in the treatment of many eye diseases, including epimacular membranes, diabetic retinopathy, vitreous hemorrhage, macular hole, detached retina, and complications of cataract surgery, among others.

During vitreoretinal surgery, an ophthalmologist typically uses a surgical microscope to view the fundus through the cornea, while surgical instruments that penetrate the sclera may be introduced to perform any of a variety of different procedures. The surgical microscope provides imaging and optionally illumination of the fundus during vitreoretinal surgery. The patient typically lies supine under the surgical microscope during vitreoretinal surgery and a speculum is used to keep the eye exposed. Depending on a type of optical system used, the ophthalmologist has a given field of view of the fundus, which may vary from a narrow field of view to a wide field of view that can extend to peripheral regions of the fundus. For many types of vitreoretinal surgery using the surgical microscope, the surgeon may desire to have a very wide field of view of the fundus that extends beyond the equator and even out to the ora serrata. The optical system to provide the view of the fundus to the surgeon during vitreoretinal surgery may include a special ocular lens, of which three types are typically used: a direct (plano, flat, or magnifying) contact lens, an indirect non-contact lens, or an indirect contact lens.

A contact lens is in physical contact with the cornea and therefore has a concave surface to match the convex surface of the cornea. Typically a small amount of refractive index-matching gel or fluid resides between the cornea and the contact lens to prevent unwanted extraneous interfacial reflections and to protect the cornea from dehydration.

A non-contact lens does not touch the eye and is spaced a certain working distance away from the eye.

A direct lens creates a non-inverted virtual image of the fundus behind the eye lens and generally in front of the fundus. The surgeon uses the surgical microscope to focus directly on this non-inverted virtual image, which is also referred to as an intermediate image plane or a focus plane. The direct lens enables the surgeon to directly view the fundus.

An indirect lens creates an inverted real image in the intermediate image plane in front of the eye lens (between the eye lens and the surgical microscope) and the surgeon uses the surgical microscope to focus on this intermediate image plane. The indirect lens enables the surgeon to indirectly view the fundus via the intermediate image plane. Since the indirect lens image is inverted to the viewer looking through the surgical microscope, typically an inverter lens is added to the surgical microscope to re-invert the fundus image to match the physical orientation of the eye during vitreoretinal surgery.

A direct contact lens can be placed onto the eye and is generally thin enough axially to normally remain in place on the cornea during vitreoretinal surgery. In certain optical systems, direct contact lenses have self-stabilizing features on the lens, such as base extensions that assist in keeping the direct contact lens from moving during surgery. However, a direct contact lens may not provide a very wide field of view into the fundus and of the retina and the field of view may be limited to about 30 degrees.

An indirect non-contact lens is not in contact with the eye and may be fixed to the surgical microscope. Therefore, the indirect non-contact lens may avoid issues of positional instability and additional resources involved (such as having a skilled surgical assistant to hold or reposition the lens) during vitreoretinal surgery. At least for these reasons, the indirect non-contact lens may be the ophthalmic surgical lens often chosen by many ophthalmologists. However, an indirect non-contact lens may be limited in the field of view of the fundus provided to the surgeon during vitreoretinal surgery. For example, the field of view using an indirect non-contact lens may be limited to less than about 140 degrees (full angle) and may be about 10 degrees less than wide angle contact lenses.

In order to see beyond the region of fundus viewable at one time with the indirect non-contact lenses, the surgeon may employ various techniques during vitreoretinal surgery. For example, the surgeon may indent a peripheral region of sclera to push the fundus in the affected region into the field of view. The surgeon may rotate the eye off the optical axis to direct the field of view onto the desired peripheral region. In some instances, a combination of techniques is used. Frequently rotating the eye or depressing the sclera to view peripheral regions of the fundus are extraneous operations during vitreoretinal surgery that are performed for the purpose of obtaining a sufficient view and do not contribute to the primary treatment purpose of the surgery. Such extraneous operations may result in additional trauma for the patient, increased time of surgery, and increased likelihood of surgical complications and may be undesirable for at least these reasons.

An indirect contact lens may provide a much greater field of view of the fundus than other types of ophthalmic surgical lenses. Indirect contact lenses may provide a field of view up to about 170 degrees (full angle), essentially out to the very edge of the retina at the ora serrata in a single image. However, indirect contact lenses, which rest on the cornea during vitreoretinal surgery, are generally top-heavy due to their optical construction and typically move in angular and positional orientation after initial placement on the eye. Indirect contact lenses may also be relatively sensitive to small movements by the patient during surgery, which is undesirable. Therefore, the surgeon oftentimes engages the help of an assistant, either to continually hold the indirect contact lens in place or to frequently reposition the indirect contact lens many times during the course of vitreoretinal surgery. Despite the large field of view afforded, the lack of positional stability and the additional involvement of a skilled surgical assistant to position the lens may be undesirable. At least for these reasons, the free-standing indirect contact lens may be an unpopular choice among vitreoretinal surgeons.

SUMMARY

The disclosed embodiments of the present disclosure provide for illuminating and viewing the extreme periphery of the fundus during vitreoretinal surgery without implementing extraneous operations, without using additional skilled surgical personnel, and without having the positional instability of a free-standing indirect contact lens.

In one aspect, a disclosed method for performing ophthalmic surgery includes positioning a first optical axis of a surgical microscope along a second optical axis of an eye of a patient, and viewing an interior portion of the eye using an indirect contact lens in contact with the eye. The indirect contact lens may be mechanically coupled to the surgical microscope.

In any of the disclosed embodiments, the indirect contact lens may be mechanically coupled to the surgical microscope to prevent tilting of the indirect contact lens away from the first optical axis.

In any of the disclosed embodiments, the method may further include manually lowering the indirect contact lens to be in contact with the eye. When the indirect contact lens is in contact with the eye, the method may include focusing the surgical microscope at a focus plane of the indirect contact lens.

In any of the disclosed embodiments, the indirect contact lens may be mechanically coupled to the surgical microscope to enable movement of the indirect contact lens with respect to the surgical microscope in a direction corresponding to the first optical axis.

In any of the disclosed embodiments, the method may further include mechanically coupling the indirect contact lens to the surgical microscope using a surgical microscope attachment. In the method, the indirect contact lens may be mechanically coupled to the surgical microscope to enable rotation about a mounting member of the surgical microscope attachment. In the method, the indirect contact lens may be mechanically coupled to the surgical microscope to enable horizontal translation with respect to the mounting member. In the method, the mounting member may enable movement of the indirect contact lens with respect to the surgical microscope in a direction corresponding to the first optical axis.

In another aspect, a surgical microscope attachment may include a mounting member for mounting the surgical microscope attachment to a surgical microscope having an optical axis. The surgical microscope attachment may include an extension member coupled to the mounting member. In the surgical microscope attachment, the extension member may translate with respect to the mounting member in a first direction aligned with the optical axis. The surgical microscope attachment may include a lens holder coupled to the extension member to position an indirect contact lens for viewing an eye of a patient during ophthalmic surgery using the surgical microscope. In the surgical microscope attachment, the lens holder may rotate with respect to the extension member and may translate with respect to the extension member in a second direction perpendicular to the optical axis.

In any of the disclosed embodiments, the surgical microscope attachment may include a first bearing coupling the mounting member to the extension member, the first bearing for reducing friction when the extension member translates in the first direction.

In any of the disclosed embodiments, the surgical microscope attachment may include a second bearing coupling the extension member to the lens holder, the second bearing for reducing friction when the lens holder rotates about the extension member.

In any of the disclosed embodiments, the surgical microscope attachment may include a third bearing coupling the extension member to the lens holder, the third bearing for reducing friction when the lens holder translates with respect to the extension member in the second direction.

In any of the disclosed embodiments, the lens holder may further include a coupling member that includes the second bearing and the third bearing, an arm member that runs linearly in the third bearing at a first end and that couples to the indirect contact lens at a second end, and a retaining mechanism at the second end of the arm member to attach the indirect contact lens to the lens holder.

In any of the disclosed embodiments, the surgical microscope attachment may include a detention mechanism to prevent the extension member from uncoupling from the mounting member. In the surgical microscope attachment, the detention mechanism may detain the extension member at a maximum translation in the first direction with respect to the mounting member. In the surgical microscope attachment, a range of translation in the first direction of the extension member may enable an objective of the surgical microscope to focus at a focal plane of the indirect contact lens.

In any of the disclosed embodiments of the surgical microscope attachment, the mounting member and the extension member may be cylindrically shaped and may be arranged concentrically to each other at a center line. In the surgical microscope attachment, the lens holder may rotate about the center line. In the surgical microscope attachment, the lens holder may prevent tilting of the indirect contact lens away from the optical axis.

BRIEF DESCRIPTION OF THE DRAWINGS

For a more complete understanding of the present invention and its features and advantages, reference is now made to the following description, taken in conjunction with the accompanying drawings, in which.

DESCRIPTION OF PARTICULAR EMBODIMENT(S)

Figure 1:
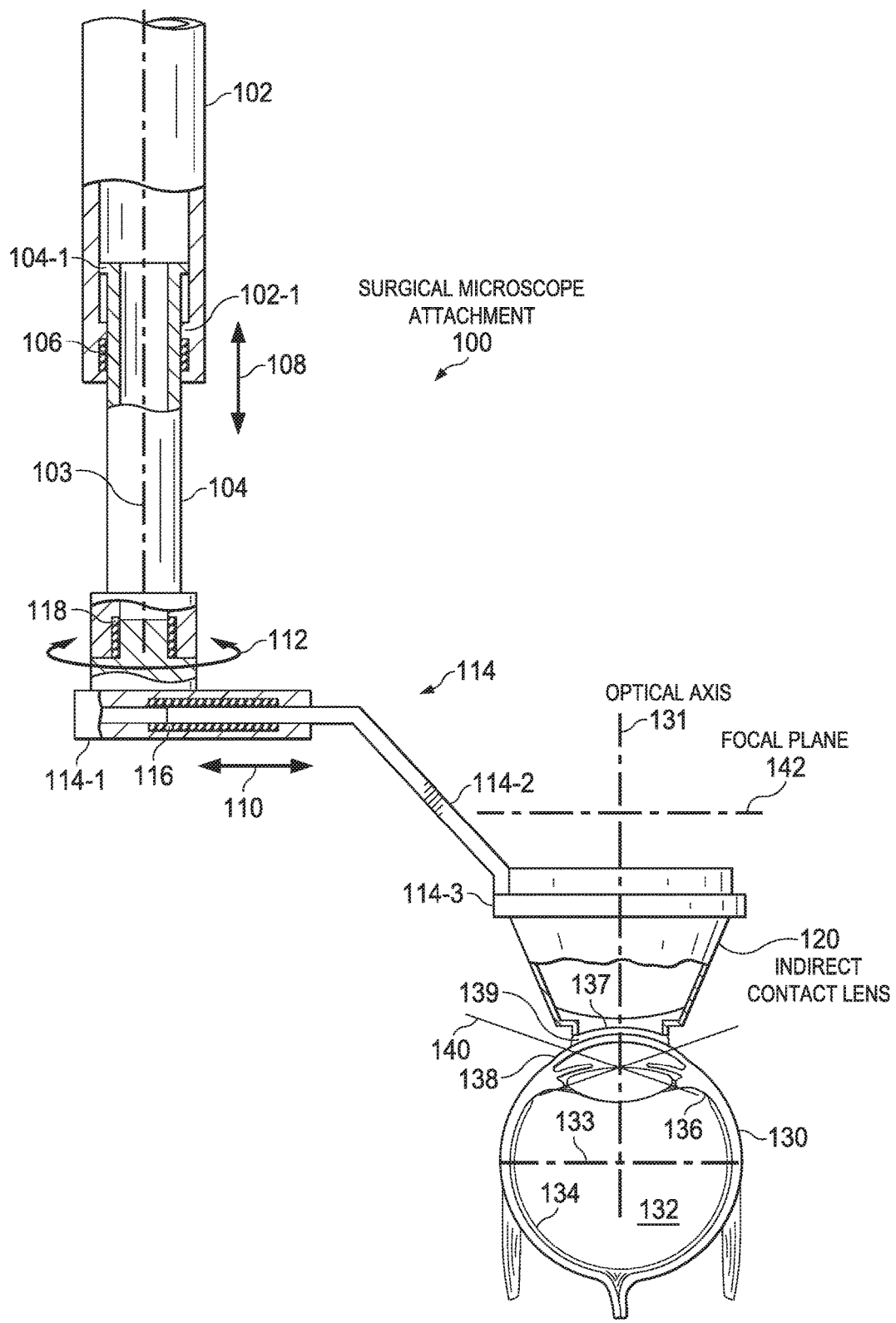
FIG. 1 is a lateral view of selected elements of an embodiment of a surgical microscope attachment for supporting an indirect contact lens.

In the following description, details are set forth by way of example to facilitate discussion of the disclosed subject matter. It should be apparent to a person of ordinary skill in the field, however, that the disclosed embodiments are exemplary and not exhaustive of all possible embodiments.

As used herein, a hyphenated form of a reference numeral refers to a specific instance of an element and the un-hyphenated form of the reference numeral refers to the collective element. Thus, for example, device '12-1' refers to an instance of a device class, which may be referred to collectively as devices '12' and any one of which may be referred to generically as a device '12'.

As noted above, free-standing indirect contact lenses, though they provide a much greater field of view of the fundus than other types of ophthalmic surgical lenses, are not frequently used by surgeons during vitreoretinal surgery. Because indirect contact lenses are top heavy in construction, such lenses may exhibit positional instability when resting on the cornea of a patient during surgery. Indirect contact lenses may easily lose angular and positional orientation after initial placement on the eye, resulting in repeated or continuous manual effort for repositioning during surgery. Furthermore, the instability of a typical indirect contact lens may be unpredictable during surgery, which is also undesirable.

As will be described in further detail, the inventors of the present disclosure have developed a surgical microscope attachment for mechanically supporting an indirect contact lens by a surgical microscope used during ophthalmic surgery. The surgical microscope attachment disclosed herein may force the indirect contact lens to remain upright, and hence remain aligned with an optical axis of the eye of the patient, during surgery. The surgical microscope attachment disclosed herein may further enable the indirect contact lens to move without substantial mechanical resistance in the horizontal and vertical direction (within certain limits) to conform to the position of the eye during surgery. In this manner, the surgical microscope attachment disclosed herein may provide positional stability for the indirect contact lens, while retaining a certain amount of flexibility in movement, such as from small movements of the patient during surgery. Accordingly, the surgical microscope attachment disclosed herein may enable the ophthalmic surgeon to enjoy the wide angle viewing capabilities afforded by indirect contact lenses, without the positional instability problems of a free-standing indirect contact lens without mechanical support, such as using additional skilled surgical personnel, and without implementing extraneous operations during surgery, such as rotating the eye or indenting the sclera to view desired portions of the fundus.

Referring now to the drawings, FIG. 1 illustrates a lateral view of selected elements of an embodiment of a surgical microscope attachment 100 for supporting an indirect contact lens. FIG. 1 is a lateral view with partial cross-sectional views and is a schematic drawing that is not drawn to scale. As will be described in further detail, FIG. 1 shows surgical microscope attachment 100 fixed to an indirect contact lens 120 that rests on an eye 130. Surgical microscope attachment 100, as shown, is comprised of a mounting member 102, an extension member 104, and a lens holder 114. As shown, lens holder 114 includes a coupling member 114-1, an arm member 114-2, and a retaining mechanism 114-3. In various embodiments, surgical microscope attachment 100 may be implemented with fewer or more components than illustrated in the exemplary embodiment of FIG. 1, which is shown for descriptive purposes.

Figure 2:
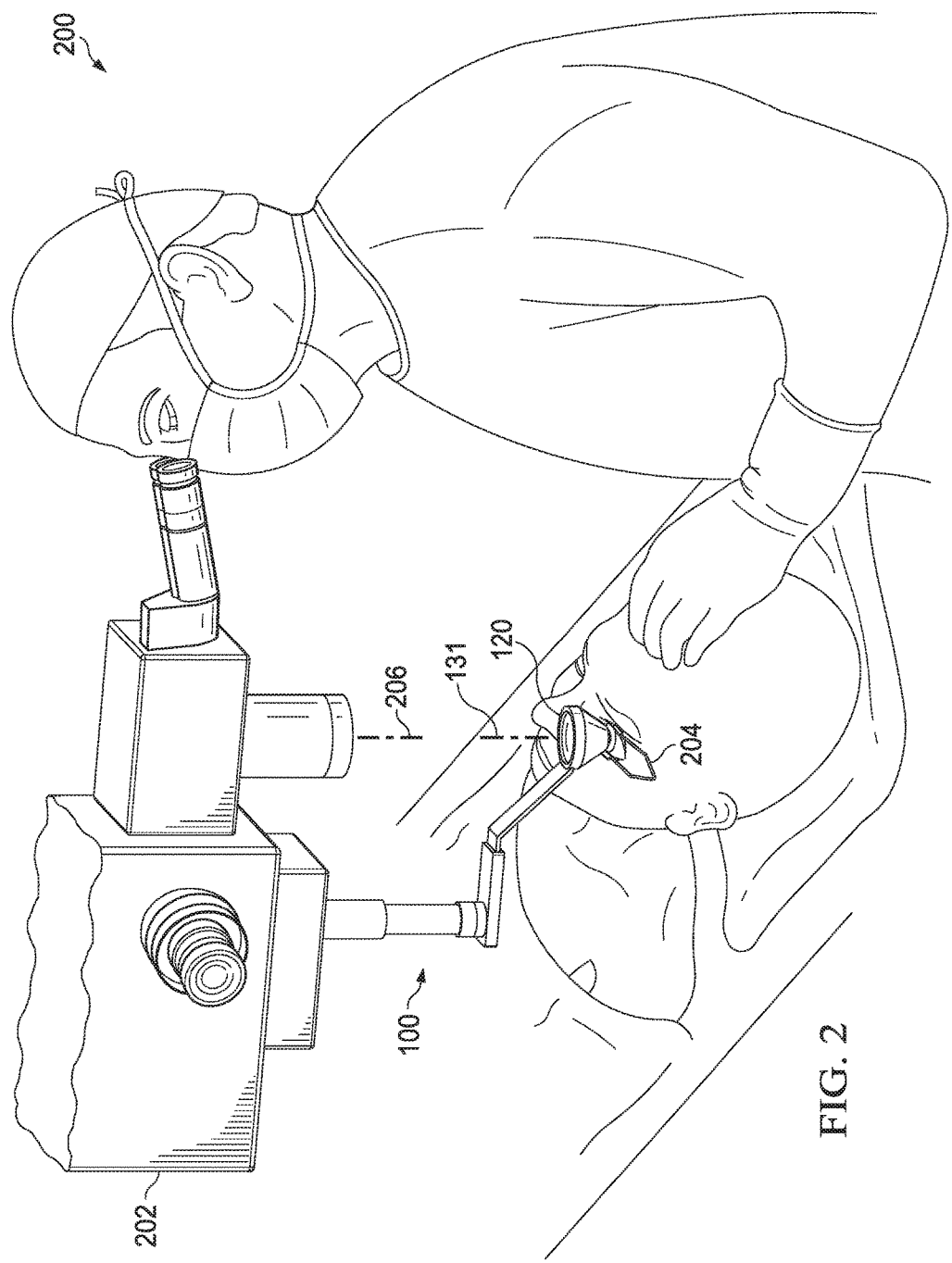
FIG. 2 is a depiction of an embodiment of a vitreoretinal surgery using a surgical microscope and a surgical microscope attachment for supporting an indirect contact lens.

In FIG. 1, surgical microscope attachment 100 includes mounting member 102 for mounting to a surgical microscope (see FIG. 2). Mounting member 102 may be any of a variety of structural members used for mechanical attachment, such a tube, rod, beam, channel, or other type of structural member. As shown, mounting member 102 is a hollow cylindrical (or tube) member having center line 103. Although a mounting point of mounting member 102 to the surgical microscope is omitted from view in FIG. 1 for clarity, it will be understood that surgical microscope attachment 100 may be mounted to the surgical microscope to enable an objective of the surgical microscope to view an indirect image generated by indirect contact lens 120, and to focus on a focal plane 142 where the indirect image is generated.

As shown, mounting member 102 is concentrically coupled to extension member 104 about center line 103, where extension member 104 is also shown as a hollow cylindrical (or tube) member. When mounting member 102 has another shape, such as a hollow square or rectangular cross-section, for example, extension member 104 may be correspondingly shaped to mate or couple with mounting member 102. Extension member 104 is able to translate vertically in direction 108 with respect to mounting member 102.

As shown in FIG. 1, extension member 104 is telescopically coupled to mounting member 102 about center line 103. Between extension member 104 and mounting member 102, bearings 106 may enable extension member 104 to run in direction 108 with very low friction. Additionally, a detention mechanism may prevent extension member 104 from dropping out of mounting member 102. Specifically, extension member 104 may have a flange 104-1 that abuts on ring 102-1 of mounting member 102 to prevent extension member 104 from falling out. Other detention mechanisms may be used in different embodiments. In this manner, extension member 104 may be detained at a maximum vertical translation with respect to mounting member 102, but may travel freely in direction 108 at other positions with very low friction.

In FIG. 1, lens holder 114 is mounted to the other end of extension member 104. Lens holder 114 may be rotatably coupled to extension member 104 at coupling member 114-1 by means of bearing 118. Coupling member 114-1 may be fixed to extension member 104 to prevent any movement, other than the rotation enabled by bearing 118, therebetween. Bearing 118 may enable rotation with very low friction about center line 103, shown by rotational direction 112. In various embodiments, bearing 118 may enable full 360 degrees of rotation without limit. As coupling member 114-1 rotates using bearing 118, lens holder 114, including arm member 114-2 and retaining mechanism 114-3, rotates correspondingly. At small angles of rotation enabled by bearing 118, indirect contact lens 120, when mounted to surgical microscope attachment 100, may be enabled to move horizontally in a direction perpendicular to the page of FIG. 1.

In FIG. 1, coupling member 114-1 further includes bearing 116 that provides linear movement of arm member 114-2 with very low friction. As shown, the linear movement of arm member 114-2 enabled by bearing 116 is in direction 110 that is parallel to the page of FIG. 1. More generally, arm member 114-2 is enabled to translate radially with respect to center line 103. Arm member 114-2 may be detained within coupling member 114-1 at one end using any of a variety of detention mechanisms (not shown). In some embodiments, one end of arm member 114-2 may be freely removed from, or inserted into, coupling member 114-1 without a detention mechanism. When mounted to surgical microscope attachment 100, arm member 114-2 may enable indirect contact lens 120 to move horizontally in the radial direction with respect to center line 103. At another end of arm member 114-2, retaining mechanism 114-3 enables attachment of indirect contact lens 120 to surgical microscope attachment 100, and accordingly, to the surgical microscope. As shown, retaining mechanism 114-3 may be a ring clip that encompasses indirect contact lens 120 and is fixed to indirect contact lens 120. In other embodiments, retaining mechanism 114-3 may be a different type of mechanical coupling mechanism, such as a threaded rod or hole, a clip, an insert, etc., for coupling indirect contact lens 120 in a fixed manner to arm member 114-2. It is noted that different types of retaining mechanism 114-3, to enable use of different types of indirect contact lens 120, including commercially available indirect contact lenses, may be included with surgical microscope attachment 100.

Thus as shown in FIG. 1, indirect contact lens 120 is mechanically coupled to the surgical microscope using surgical microscope attachment 100 but is still afforded a certain degree of horizontal and vertical motion with very low friction. Surgical microscope attachment 100 may be used to safely place indirect contact lens 120 on eye 130 during vitreoretinal surgery and hold indirect contact lens 120 in alignment with an optical axis of the surgical microscope (see also FIG. 2), which may be aligned with optical axis 131 of eye 130. Even when optical axis 131 deviates slightly from the optical axis of the surgical microscope during vitreoretinal surgery, surgical microscope attachment 100 may still enable useful imaging of the fundus by keeping indirect contact lens 120 aligned with the optical axis of the surgical microscope. In other words, even when optical axis 131 of the eye tilts away from the optical axis of the surgical microscope during vitreoretinal surgery, surgical microscope attachment 100 may enable the surgeon to continue viewing the fundus with a wide angle view using indirect contact lens 120. Furthermore, surgical microscope attachment 100 may enable the surgeon to continue viewing the fundus without significant risk of injury to the patient that might otherwise result from an optical arrangement that is fixed and does not afford any motion of an ocular lens.

Specifically, indirect contact lens 120 may include a concave portion 137 that mates with the convex shape of cornea 138 where optical coupling agent 139 is used. Optical coupling agent 139 may be applied as a film interfacial layer to prevent unwanted reflections and to enable viewing into eye 130 along optical axis 131. The indirect image generated by indirect contact lens 120 at focal plane 142 may correspond to a field of view 140 that is relatively wide and may extend out beyond eye equator 133 to the ora serrata 136 where retina 134 ends. Thus, field of view 140 includes a large portion of the fundus that is filled with vitreous humor 132, including all or most of retina 134. In this manner, the surgeon is afforded a safe and stable view to perform any of a variety of surgical techniques on eye 130. Furthermore, surgical microscope attachment 100 may enable relatively quick removal and replacement of indirect contact lens 120 on eye 130, even during surgery, as desired.

Modifications, additions, or omissions may be made to surgical microscope attachment 100 without departing from the scope of the disclosure. The components and elements of surgical microscope attachment 100, as described herein, may be integrated or separated according to particular applications. Surgical microscope attachment 100 may be implemented using more, fewer, or different components in some embodiments.

Turning now to FIG. 2, a depiction of an embodiment of a vitreoretinal surgery 200 using a surgical microscope 202 and surgical microscope attachment 100 for supporting indirect contact lens 120 is shown. In FIG. 2, the use of surgical microscope attachment 100 as shown in FIG. 1 with a patent and a surgeon is depicted. Although FIG. 2 is shown with surgical microscope 202 above the patient, it is noted that different orientations of the patient with respect to surgical microscope 202 may be practiced in different embodiments.

The patient has an eye exposed using speculum 204 that is in contact with indirect contact lens 120, while the surgeon is viewing the fundus of the patient's eye using surgical microscope 202. As a result of bearings 106, 118, and 116, explained above with respect of FIG. 1, which provide low friction movement, very little vertical or horizontal pressure is extorted on the eye of the patient in vitreoretinal surgery 200. Because indirect contact lens 120 still rests freely on the cornea, indirect contact lens 120 may be self-retaining due to the weight of indirect contact lens 120 transmitted to convex portion 137, which resists lateral sliding of indirect contact lens 120 relative to the cornea. Therefore, when the patient's eye moves slightly relative to surgical microscope 202, indirect contact lens 120 stays with the patient's eye and may move relative to surgical microscope 202. However, as explained previously, surgical microscope attachment 100 maintains alignment of indirect contact lens 120 with an optical axis 206 of surgical microscope 202, thereby enabling useful imaging for the surgeon to be maintained during surgery without external intervention, such as by a skilled surgical technician.

When indirect contact lens 120 is initially placed on the eye, optical axis 131 of the eye will generally be aligned with optical axis 206 of surgical microscope 202. However, when the patient makes a small movement during surgery, such as a lateral or vertical movement of the head, optical axis 131 may become slightly non-aligned with optical axis 206. Even when optical axis 206 is no longer perfectly aligned with optical axis 131, surgical microscope attachment 100 may keep indirect contact lens 120 aligned with optical axis 206 to enable useful viewing of the fundus during surgery without interruption. In this manner using surgical microscope attachment 100, as disclosed herein, extraneous operations to view peripheral regions of the fundus may be avoided, and additional personnel or manual actions to maintain the positional stability of indirect contact lens 120 may be eliminated.

The objective used with surgical microscope 202 may have a focal length of about 175 mm to 225 mm that focuses on focal plane 142 of indirect contact lens 120. It is noted that surgical microscope 202 may provide illumination for the fundus that is projected through indirect contact lens 120. Thus the surgeon may be provided with field of view 140 (see FIG. 1) via surgical microscope 202 and may safely proceed with any of a variety of vitreoretinal surgical procedures (not shown).

Figure 3:
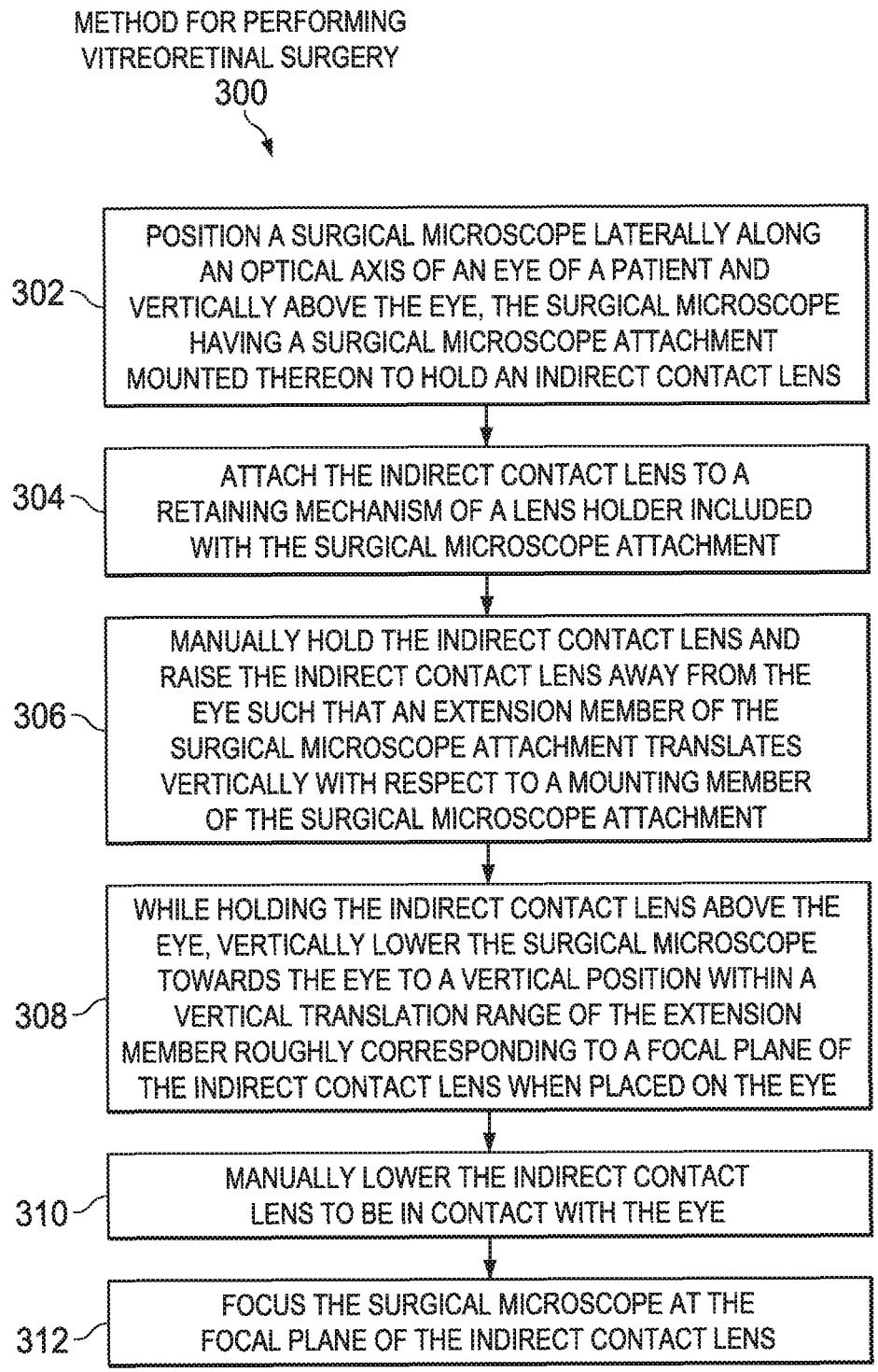
FIG. 3 is a flow chart of selected elements of a method for performing vitreoretinal surgery.

Referring now to FIG. 3, a flow chart of selected elements of an embodiment of a method 300 for performing vitreoretinal surgery, as described herein, is depicted in flowchart form. Method 300 describes steps and procedures for using surgical microscope attachment 100 with indirect contact lens 120 (see FIGS. 1 and 2) to view the fundus of an eye and to enable further surgical procedures based on the view of the fundus. It is noted that certain operations described in method 300 may be optional or may be rearranged in different embodiments. Method 300 may be performed by a surgeon or by other medical personnel. In some embodiments, at least certain portions of method 300 may be automated, for example using servo-mechanical control associated with certain aspects of the surgical microscope, such as raising or lowering the surgical microscope.

Method 300 may begin, at step 302, by positioning a surgical microscope laterally along an optical axis of an eye of a patient and vertically above the eye, the surgical microscope having a surgical microscope attachment mounted thereon to hold an indirect contact lens. In certain embodiments of step 302, the patient is moved relative to the surgical microscope. Then, at step 304, the indirect contact lens is fixed to a retaining mechanism of a lens holder included with the surgical microscope attachment. At step 306, the indirect contact lens is held manually and is raised away from the eye such that an extension member of the surgical microscope attachment translates vertically with respect to a mounting member of the surgical microscope attachment. While holding the indirect contact lens above the eye, at step 308, the surgical microscope is vertically lowered towards the eye to a vertical position within a vertical translation range of the extension member roughly corresponding to a focal plane of the indirect contact lens when placed on the eye. At step 310, the indirect contact lens is manually lowered to be in contact with the eye. An optical coupling agent may be applied at step 310 (or prior to step 310) between the indirect contact lens and the cornea of the eye. At step 312, the surgical microscope is focused at the focal plane of the indirect contact lens. After step 312, the surgeon may view the fundus of the eye using the indirect contact lens and proceed with any of a variety of surgical procedures.

As disclosed herein, an indirect contact lens is mechanically coupled to a surgical microscope during ophthalmic surgery, such as vitreoretinal surgery. The indirect contact lens rests on a cornea of an eye of a patient during the surgery but is supported by a surgical microscope attachment having multiple degrees of freedom to accommodate small movements of the eye while remaining aligned to an optical axis of the surgical microscope.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A method for performing ophthalmic surgery using surgical microscopes, the method comprising:
   positioning a first optical axis of a surgical microscope along a second optical axis of an eye of a patient;
   lowering an indirect contact lens to be in contact with the eye, wherein the indirect contact lens is held by a lens holder attached to the surgical microscope with a cylindrical mounting portion concentrically oriented to a cylindrical extension portion, wherein the cylindrical extension portion is configured to translate with respect to the cylindrical mounting portion in a first direction parallel to the first optical axis and in a third direction opposite to the first direction;
   viewing an interior portion of the eye using the indirect contact lens in contact with the eye, wherein the lens holder rotates with respect to the cylindrical extension portion and the lens holder translates with respect to the cylindrical extension portion in a second direction perpendicular to the first optical axis and in a fourth direction opposite to the second direction;
   wherein a first bearing is disposed between the cylindrical mounting portion and the cylindrical extension portion, the first bearing configured to assist the cylindrical extension portion to translate in the first direction and in the third direction; and
   wherein the cylindrical extension portion is configured to translate freely with respect to the cylindrical mounting portion in the first direction and the third direction, and wherein the cylindrical extension portion, the lens holder, and the indirect contact lens are configured to be freely supported by the eye when the indirect contact lens is in contact with the eye.

2. The method of claim 1, wherein the lens holder prevents tilting of the indirect contact lens away from the first optical axis.

3. The method of claim 1, further comprising:
   when the indirect contact lens is in contact with the eye, focusing the surgical microscope at a focus plane of the indirect contact lens.

4. The method of claim 1, wherein the first bearing enables translation of the indirect contact lens along the first optical axis with respect to the cylindrical mounting portion.

5. The method of claim 1, wherein a second bearing is disposed between the cylindrical extension portion and the lens holder, the second bearing assisting the lens holder to rotate about the cylindrical extension portion.

6. The method of claim 5, wherein the lens holder rotates about a centerline of the cylindrical extension portion.

7. The method of claim 1, wherein a third bearing is disposed between the cylindrical extension portion and the lens holder, the third bearing enabling the lens holder to translate with respect to the cylindrical extension portion in the second direction and the fourth direction.

8. The method of claim 7, further comprising:
   using a coupling portion that includes a second bearing and the third bearing to couple the lens holder to the cylindrical extension portion, wherein an arm runs linearly in the third bearing at a first end and couples to the indirect contact lens at a second end, and wherein a retaining band at the second end of the arm fixes the indirect contact lens to the lens holder.

9. The method of claim 1, further comprising:
   preventing the cylindrical extension portion from uncoupling from the cylindrical mounting portion using a flange at one end of the cylindrical extension portion, wherein the flange detains the cylindrical extension portion at a maximum translation in the first direction with respect to the cylindrical mounting portion.

10. The method of claim 9, wherein a range of translation in the first direction of the cylindrical extension portion enables an objective of the surgical microscope to focus at a focal plane of the indirect contact lens.

11. The method of claim 1, further comprising:
    securing the indirect contact lens with the lens holder, wherein a third optical axis of the indirect contact lens is held parallel to the first optical axis.

12. The method of claim 1, wherein the cylindrical extension portion concentrically oriented to the cylindrical mounting portion further comprises:
    the cylindrical extension portion concentrically oriented to the cylindrical mounting portion within a hollow interior of the cylindrical mounting portion.

* * * * *